United States Patent
Luo

(10) Patent No.: US 12,403,279 B1
(45) Date of Patent: Sep. 2, 2025

(54) NOISE-REDUCING RESPIRATORY DEVICE

(71) Applicant: WALLENBERG UNION LLC, Newark, DE (US)

(72) Inventor: David Luo, Newark, DE (US)

(73) Assignee: WALLENBERG UNION LLC, Newark, DE (US)

( * ) Notice: Subject to any disclaimer, the term of this patent is extended or adjusted under 35 U.S.C. 154(b) by 0 days.

(21) Appl. No.: 18/784,500

(22) Filed: Jul. 25, 2024

(51) Int. Cl.
*A61M 16/00* (2006.01)
*A61M 16/10* (2006.01)

(52) U.S. Cl.
CPC .... *A61M 16/0066* (2013.01); *A61M 16/0003* (2014.02); *A61M 16/10* (2013.01); *A61M 2202/0007* (2013.01); *A61M 2202/02* (2013.01); *A61M 2205/0216* (2013.01); *A61M 2205/025* (2013.01); *A61M 2205/103* (2013.01); *A61M 2205/3331* (2013.01); *A61M 2205/42* (2013.01)

(58) Field of Classification Search
CPC ............ A61M 16/0066; A61M 16/003; A62M 2205/42
See application file for complete search history.

(56) References Cited

U.S. PATENT DOCUMENTS

| 5,397,950 A | 3/1995 | Norbury, Jr. et al. |
|---|---|---|
| 2005/0103339 A1 | 5/2005 | Daly et al. |
| 2007/0277827 A1* | 12/2007 | Bordewick ....... A61M 16/1075 128/205.25 |
| 2008/0304986 A1 | 12/2008 | Kenyon et al. |
| 2009/0007912 A1 | 1/2009 | Lindell et al. |
| 2010/0307498 A1 | 12/2010 | Jones et al. |
| 2012/0167879 A1* | 7/2012 | Bowman ........... A61M 16/0655 128/205.12 |
| 2013/0263854 A1 | 10/2013 | Taylor et al. |
| 2013/0306072 A1* | 11/2013 | Moir ..................... F04D 29/048 415/203 |
| 2014/0158131 A1 | 6/2014 | Kenyon et al. |
| 2014/0299130 A1 | 10/2014 | Librett et al. |
| 2014/0299132 A1 | 10/2014 | Librett et al. |
| 2015/0059745 A1 | 3/2015 | Barker et al. |

(Continued)

FOREIGN PATENT DOCUMENTS

| CN | 104132003 | 11/2014 |
|---|---|---|
| CN | 117145810 | 12/2023 |

(Continued)

*Primary Examiner* — Margaret M Luarca
(74) *Attorney, Agent, or Firm* — HSML P.C.

(57) ABSTRACT

A noise-reducing respiratory device configured to improve or treat respiratory system-related disorders such as sleep apnea. The device includes a noise-reducing gas passage located inside a casing of the device, and is connected to the casing. The casing of the respiratory device also has at least one air intake and at least one air outlet. The air intake is configured to receive breathable gas into the chambers of the noise-reducing gas passage. The air outlet is configured on one side to communicate with an outlet of the blower, and on the other side, it connects to a breathing hose. Additionally, electronic components and a soundproofing material are provided between the noise-reducing gas passage and the casing of the device. Furthermore, there is no foam present where the internal gas flows through the respiratory device.

20 Claims, 16 Drawing Sheets

(56) References Cited

U.S. PATENT DOCUMENTS

| | | | |
|---|---|---|---|
| 2015/0320960 A1* | 11/2015 | Barlow | A61M 16/021 128/205.25 |
| 2020/0188616 A1 | 6/2020 | Kenyon et al. | |
| 2023/0398318 A1 | 12/2023 | Mazzone | |
| 2024/0207545 A1 | 6/2024 | Chen et al. | |

FOREIGN PATENT DOCUMENTS

| | | |
|---|---|---|
| CN | 117553038 | 2/2024 |
| WO | 2024017377 | 1/2024 |

* cited by examiner

NOISE-REDUCING RESPIRATORY DEVICE

TECHNICAL FIELD

This disclosure relates to a noise-reducing respiratory device configured to improve or treat respiratory system-related disorders such as sleep apnea.

BACKGROUND

Sleep plays a crucial role in promoting physical and mental health. Problems with sleep quality, duration, and frequency can severely disrupt normal bodily, psychological, social, and emotional functions; these issues are caused by sleep disorders, which affect millions of people worldwide. Approximately 50 to 70 million people in the United States suffer from chronic sleep or wakefulness disorders, such as narcolepsy, insomnia, and sleep apnea. Among these, narcolepsy is characterized by excessive daytime sleepiness and brief, involuntary episodes of sleep that can severely interfere with daily activities, including work or social interactions. Additionally, about 70% of patients experience sudden losses of muscle strength, known as cataplexy attacks. Moreover, sleep disorders can occur at any age but are especially prevalent in middle-aged men. They are extremely detrimental to individuals' physical and mental health and can even lead to the development of multiple complications such as depression, bipolar disorder, and schizophrenia. Snoring is often a primary symptom of these conditions. Given the severe impact of sleep disorders, diagnosing them is crucial to protecting health in a timely manner.

People breathe through their nose and mouth, but during sleep, various causes can lead to the narrowing of the airways. When air passes through these narrowed passages, snoring occurs. When the cause of the airway narrowing is in the nose, it is referred to as "nasal snoring," and when it occurs in the mouth, due to the tongue or tonsils, it is known as "throat snoring." The main causes of nasal snoring are colds and allergic rhinitis, which lead to so-called nasal congestion. When the nasal mucosa becomes inflamed and the nasal airway narrows, sound is produced. Some people have a deviated septum, where the bone in the middle of the nose is bent, which also contributes to snoring. If the tonsils are enlarged or inflamed due to illness, snoring can also occur. In most cases, nasal snoring can be cured by suppressing the inflammation causing the nasal congestion, and if necessary, correcting a deviated septum to cure snoring. However, throat snoring requires careful attention as it can lead to sleep apnea, a condition where breathing repeatedly stops during sleep, typically requiring interventional treatment. Additionally, some people snore with their mouths closed; these individuals may have sleep apnea and are at risk of severe illnesses.

In summary, the causes of respiratory system-related disorders are varied, including physical constitution, fatigue, and acute physical conditions that can temporarily narrow the airway. However, in most cases, once the underlying problem is resolved, symptoms related to respiratory disorders will cease. Results from trials and data analysis show that for most adults, including the elderly, treating the respiratory tract can reduce the risk of breathing events during sleep, reduce daytime sleepiness, lower the risk of motor vehicle accidents, and improve systemic circulation blood pressure, symptoms of gastroesophageal reflux, blood sugar control in diabetic patients, and quality of life.

Therefore, by providing a steady airflow to the respiratory tract, keeping it open, and preventing the collapse and obstruction of the airway due to muscle relaxation and the inability of the soft tissues in the pharynx to support themselves while lying on the back, this method not only improves snoring but also reduces the health risks associated with obstructive sleep apnea. Recognizing and adopting effective pressure therapy to improve respiratory issues and enhance overall quality of life is both important and urgent.

SUMMARY

The objective of this disclosure is to provide a new type of noise-reducing respiratory device that not only achieves noise reduction but also ensures the health and safety of patients, facilitating the manufacture of respiratory devices and their rapid adaptation to the market. The noise-reducing respiratory device, with an interior space of the noise-reducing gas passage that does not include foam, can be used by patients over long periods and extended phases, overcoming the limitations present in similar products of current technology. Thus, it offers a more effective solution with broader application scenarios and spaces, employing a safer method to supply continuous breathable positive pressure gas to the patient's airway for the treatment of sleep-related breathing disorders.

This disclosure provides a noise-reducing respiratory device for providing continuous breathable positive pressure gas to a patient to treat respiratory system-related disorders such as sleep apnea. The noise-reducing respiratory device includes a casing that includes at least one air intake and at least one air outlet; a blower that has an inlet and an outlet, configured to continuously pressurize the breathable gas entering an interior of the noise-reducing respiratory device to form breathable positive pressure gas; and a noise-reducing gas passage configured to accommodate the blower, the noise-reducing gas passage being sealably connectable to the casing through a sealing component. The at least one air intake is configured to receive the breathable gas into the noise-reducing gas passage to supply the blower to generate the continuous breathable positive pressure gas, and the at least one air outlet is configured on one side to communicate with the outlet of the blower, and configured on another side to connect to a breathing hose to provide the continuous breathable positive pressure gas to the patient's airway. The noise-reducing respiratory device further includes electronic components provided between the casing and the noise-reducing gas passage. In addition, a soundproofing material is provided between the noise-reducing gas passage and the casing.

In one embodiment, the noise-reducing gas passage includes a first chamber and a second chamber.

In one embodiment, the blower is provided in the first chamber.

In one embodiment, the inlet of the blower is parallel or perpendicular to an axis of the at least one air intake.

In one embodiment, the soundproofing material includes one of foam, rubber, or silicone.

In one embodiment, the noise-reducing gas passage and the casing form a space through which the breathable gas flows.

This disclosure provides another noise-reducing respiratory device for providing continuous breathable positive pressure gas to a patient to treat respiratory system-related disorders such as sleep apnea. The noise-reducing respiratory device includes: a casing that includes at least one air intake and at least one air outlet; a blower that has an inlet and an outlet, configured to continuously pressurize breathable gas entering an interior of the device to form the breathable positive pressure gas; and a noise-reducing gas passage configured to accommodate the blower and be connectable to the casing. The at least one air intake is configured to receive the breathable gas into the noise-reducing gas passage to supply the blower to generate the continuous breathable positive pressure gas, and the at least one air outlet is configured on one side to communicate with the outlet of the blower, and configured on another side to connect to a breathing hose to provide the breathable positive pressure gas to the patient's airway.

The noise-reducing respiratory device further includes electronic components provided between the casing and the noise-reducing gas passage, and a soundproofing material is provided between the noise-reducing gas passage and the casing. The soundproofing material including foam has at least one of the following characteristics:

a. a thickness between 3 mm to 25 mm;
b. a hardness between 20 F to 150 F;
c. a density between 35 kg/m$^3$ to 150 kg/m$^3$.

In one embodiment, an axis of the at least one air intake of the casing is not on a same horizontal plane as an axis of the at least one air outlet.

In one embodiment, multiple layers of the soundproofing material are provided between the noise-reducing gas passage and the casing.

In one embodiment, a shortest path for the continuous breathable positive pressure gas inside the casing from the at least one air intake to the at least one air outlet is at least 160 mm.

In one embodiment, the casing includes one of the following materials: polypropylene, polycarbonate, polyethylene terephthalate-1,4-cyclohexane dimethanol ester, or polyamide.

This disclosure provides yet another noise-reducing respiratory device for providing continuous breathable positive pressure gas to a patient to treat respiratory system-related disorders such as sleep apnea. The noise-reducing respiratory device includes a casing that includes at least one air intake and at least one air outlet; a blower that has an inlet and an outlet, configured to continuously pressurize breathable gas entering an interior of the noise-reducing respiratory device to form the breathable positive pressure gas; and a noise-reducing gas passage configured to accommodate the blower and be connectable to the casing. The at least one air intake is configured to receive the breathable gas into the noise-reducing gas passage to supply the blower to generate the breathable positive pressure gas, and the at least one air outlet is configured on one side to communicate with the outlet of the blower, and on another side to connect to a breathing hose to provide the continuous breathable positive pressure gas to the patient's airway. The electronic noise-reducing respiratory device further includes electronic components provided between the casing and the noise-reducing gas passage. The interior space of the noise-reducing gas passage through which gas flows does not include foam, and a soundproofing material is provided between the noise-reducing gas passage and the casing. A ratio of an interior volume of the noise-reducing gas passage to a volume of the blower is between 3 to 18, and a ratio of an internal volume of the casing to the interior volume of the noise-reducing gas passage is between 1 to 5.

In one embodiment, the inlet of the blower is parallel or perpendicular to an axis of the at least one air intake.

In one embodiment, the respiratory device further comprises a humidifying component.

In one embodiment, the casing is configured to be divided into at least two parts, each of the at least two parts being interconnectable to form the integral casing.

In one embodiment, the axis of the at least one air intake is not on a same horizontal plane as an axis of the at least one air outlet.

This disclosure further provides a noise-reducing respiratory device for providing continuous breathable positive pressure gas to a patient to treat respiratory system-related disorders such as sleep apnea. The noise-reducing respiratory device includes: a casing that includes at least one air intake and at least one air outlet; a blower that has an inlet and an outlet, configured to continuously pressurize breathable gas entering an interior of the noise-reducing respiratory device to form the continuous breathable positive pressure gas; and a noise-reducing gas passage that is configured to accommodate the blower and be connectable to the casing. The at least one air intake is configured to receive the breathable gas into the noise-reducing gas passage to supply the blower to generate the breathable positive pressure gas, and the at least one air outlet is configured on one side to communicate with the outlet of the blower, and configured on another side to connect to a breathing hose to provide the breathable positive pressure gas to the patient's airway. The noise-reducing respiratory device further includes electronic components provided between the casing and the noise-reducing gas passage. In addition, the noise-reducing gas passage is configured to be divided into at least two chambers, with the blower housed within at least one of the at least two chambers, and an interior space of the noise-reducing gas passage through which the breathable gas flows does not include foam, and a soundproofing material is provided between the noise-reducing gas passage and the casing.

In one embodiment, a shortest path for the continuous breathable positive pressure gas inside the casing from the at least one air intake to the at least one air outlet is at least 160 mm.

In one embodiment, the noise-reducing gas passage includes one of the following materials: polypropylene, polycarbonate, polyethylene terephthalate-1,4-cyclohexane dimethanol ester, or polyamide.

In one embodiment, the soundproofing material, once molded, is provided between the noise-reducing gas passage and the casing.

In one embodiment, the casing is configured to be divided into at least two parts, each of the at least two parts being interconnectable to form the integral casing.

In one embodiment, the foam includes one of the following materials: polyurethane foam, polyester foam, polyether foam, neoprene, or cross-linked polyethylene.

The implementation of the respiratory device discussed herein offers at least the following beneficial effects:

1. The design of a foam-free noise-reducing gas passage device enhances the safety of respiratory-related devices. In 2021, a globally renowned brand issued its first worldwide recall notice involving some of its Bi-level Positive Airway Pressure (BiPAP) devices, Continuous Positive Airway Pressure (CPAP) devices, and mechanical ventilators, followed by several more recalls. The main reason for the recall was the inappropriate use of sound-absorbing foam within the noise-reducing gas passage, which could potentially release particles and organic compounds. In 2023, the FDA received thousands of complaints about this internationally known brand's CPAP and BiPAP machines. This incident had a significant negative impact on the brand's reputation.

The FDA requires that ventilators must demonstrate a noise level below 30 dB for market approval. Using foam for noise reduction is currently the simplest method because foam materials are easily obtainable and manufacturable. Their unique porous structure and material properties can convert noise into minimal energy, thereby reducing noise. Indeed, using foam to reduce noise can achieve a good noise reduction effect, and placing foam inside the noise-reducing gas passage device is the simplest, most effective, and common means to meet regulatory noise standards.

Therefore, nearly all respiratory-related machines on the current market incorporate foam within the gas passage for noise reduction. However, foam can easily cause health issues for several reasons:

A. Due to the softness and relatively loose surface of foam materials, they can be easily worn away or peeled off by airflow during use, releasing particles. Once released, these particles can easily enter the patient's airway with the airflow, irritating the respiratory system. This may cause respiratory problems, leading to symptoms such as sore throat and coughing, especially in individuals already suffering from respiratory diseases such as asthma or Chronic Obstructive Pulmonary Disease (COPD).

B. Additionally, foam is often made from synthetic materials that may contain residual chemical additives. These chemicals can gradually be released as the foam ages and degrades. In some cases, if foam particles carry harmful microbes, they could lead to potential infections, particularly in individuals with weakened immune systems. Foam particles may also trigger allergic reactions, including sneezing, flu-like symptoms, and eye irritation.

C. Furthermore, foam used over long periods can accumulate dust, bacteria, and other contaminants, especially in respiratory devices. The device can easily inhale contaminants from the air, leading to bacterial growth and increasing the risk of infection.

The disclosure discussed herein specifically focuses on the safety and reliability of the ventilator's noise-reducing gas passage during design, implementing a series of stringent safety measures, including a foam-free design of the noise-reducing gas passage device to reduce potential health risks to patients using ventilators. In designing the gas passage and filtration system, foam-free or easily replaceable foam designs are used to mitigate these potential health risks. For patient health and safety, the gas passage is configured to be foam-free. Since there is no foam in the gas passage, it reduces the chance of accumulating minute foreign objects, helping to maintain cleanliness in the gas passage. More importantly, the air breathed is not affected by minute residues from the foam itself, lowering the number of particles that patients might inhale or come into contact with, ensuring safety during device use. This is particularly important for patients who use the device over a long period as it helps to reduce potential respiratory issues. Additionally, some patients may be allergic to particles from materials such as foam, and the foam-free design reduces the risk associated with allergic reactions. This is also crucial for those allergic to foam materials or sensitive to chemically treated materials. Through multiple tests, this product has demonstrated that the foam-free noise-reducing gas passage device can enhance patient safety and comfort during device use.

2. Besides ensuring noise reduction, respiratory devices actually specify the pressure and flow of the gas blown into the patient's airway. Placing foam within the noise-reducing gas passage may cause some of the gas to be absorbed by the foam, resulting in the blown-out gas not meeting the required flow or pressure standards. The primary reasons foam can lead to inadequate pressure and flow include its porous structure, which slows down the gas velocity as it passes through the pores, increasing gas resistance and likely reducing pressure. Additionally, the foam may absorb some of the gas, thus reducing the flow rate of the gas exiting the respiratory device. Moreover, after prolonged use, the foam may become contaminated with dust, bacteria, and other substances, leading to clogged pores and further increasing airflow resistance, thus degrading the gas flow performance. Therefore, considering all these factors, this disclosure employs only the internal structure or components within the noise-reducing gas passage for noise reduction, without absorbing or obstructing the airflow. It relocates the soundproofing material from inside the air passage chamber to between the noise-reducing gas passage and the casing of the device, ensuring that the airflow does not pass through foam. In this position, the soundproofing material functions to absorb the energy and noise generated by the vibrations of the noise-reducing gas passage, thereby preventing its transmission to the casing of the device and the external environment, reducing noise disturbances to the patient. Furthermore, the soundproofing material between the casing of the device and the noise-reducing gas passage also serves to stabilize the air passage within the casing, maintaining the stability and durability of the respiratory device to ensure lasting and stable therapeutic effects. This design of placing the soundproofing material between the noise-reducing gas passage and the casing of the device not only effectively avoids obstruction of the airflow by the soundproofing material but also maximizes its noise reduction and stabilizing functions, providing patients with a quieter and more comfortable breathing environment.

3. The soundproofing material positioned between the noise-reducing gas passage and the casing of the device not only reduces noise and enhances safety but also serves multiple other functions. (1) The use of soundproofing material outside the chamber not only reduces noise and enhances safety but also provides dual-buffering shock absorption (during use and transport), offering comprehensive protection for the device's stable operation and the patient's comfort. a. Firstly, the soundproofing material between the noise-reducing gas passage and the casing of the device can serve the same function as foam inside the air passage, while also reducing the risk of gas passing through foam. The soundproofing material between the air passage and the casing allows the respiratory device to reduce noise generated by vibrations of the noise-reducing gas passage, converting sound waves into other forms of energy absorbed by the soundproofing material. Therefore, it isolates noise within the device casing, providing buffering for the noise-reducing gas passage during use. b. The soundproofing material also serves as a buffer during transport; during transportation, the device may be subjected to bumps and vibrations, and soundproofing materials (such as foam and silicone) as relatively soft materials can absorb and mitigate external shocks to some extent, protecting the internal structure of the device, especially the noise-reducing gas passage and its internal components, making the transportation of the respiratory device safer and more reliable. (2) On one hand, since breathable positive pressure gas does not pass through the soundproofing material, the selection of soundproofing material does not need to consider factors such as the potential release of harmful gases into the airflow, which broadens the range of choices for the soundproofing material and further controls the manufacturing costs of the respiratory device to some extent. (3) With foam already installed inside the noise-reducing gas passage, adding further soundproofing material between the casing of the device and the noise-reducing gas passage makes the device even quieter, surpassing regulatory noise level standards. By combining the use of foam within the noise-reducing gas passage and soundproofing material between the casing of the device and the noise-reducing gas passage, the respiratory device maintains its original functions and performance while achieving dual noise reduction, creating a more tranquil and comfortable therapeutic environment for patients.

DETAILED DESCRIPTION

Figure 1:
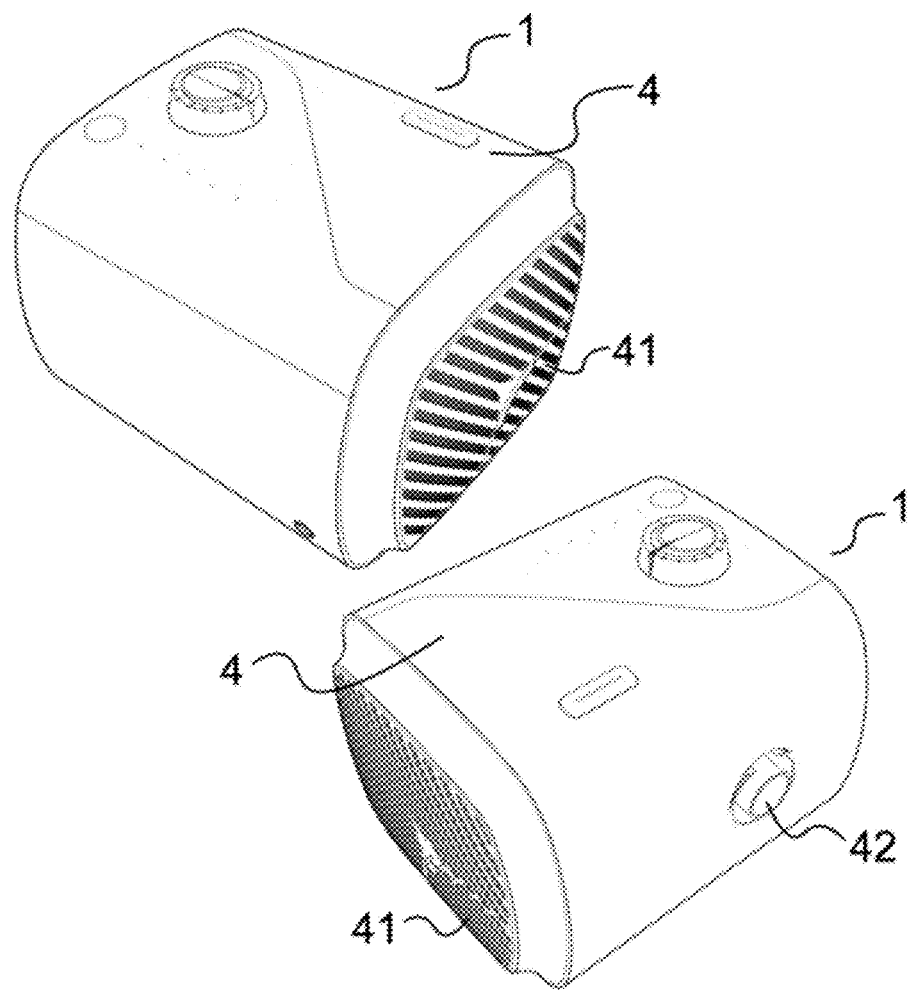
FIG. 1 is a three-dimensional schematic diagram of a noise-reducing respiratory device according to an embodiment of the present disclosure.
Figure 2:
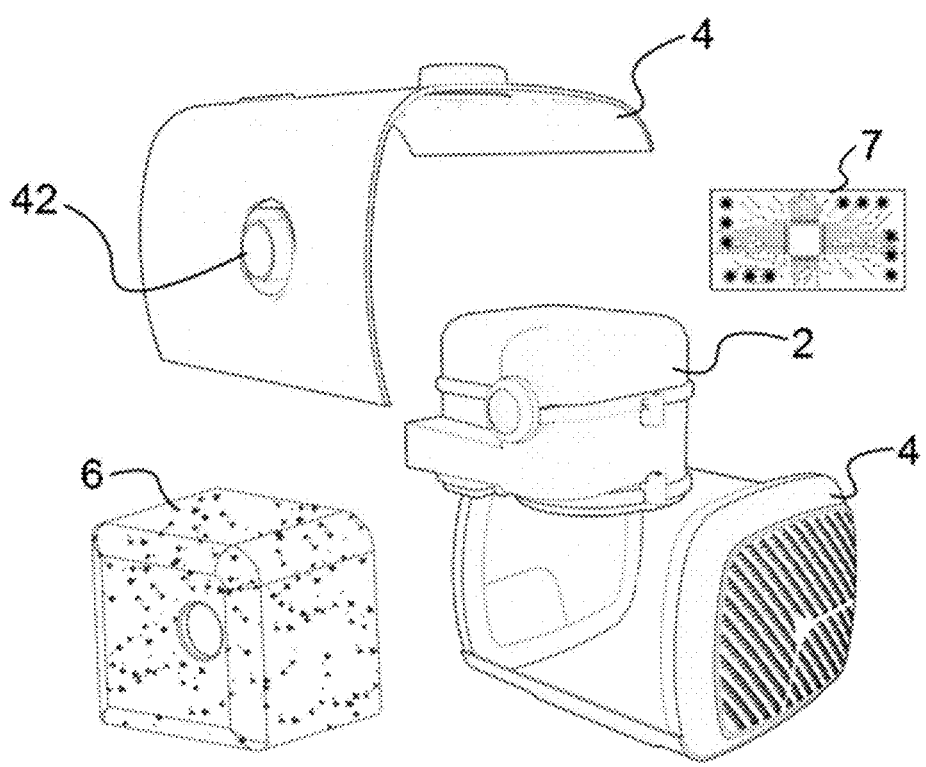
FIG. 2 is an exploded view of the structure of the noise-reducing respiratory device according to an embodiment of the present disclosure.
Figure 3:
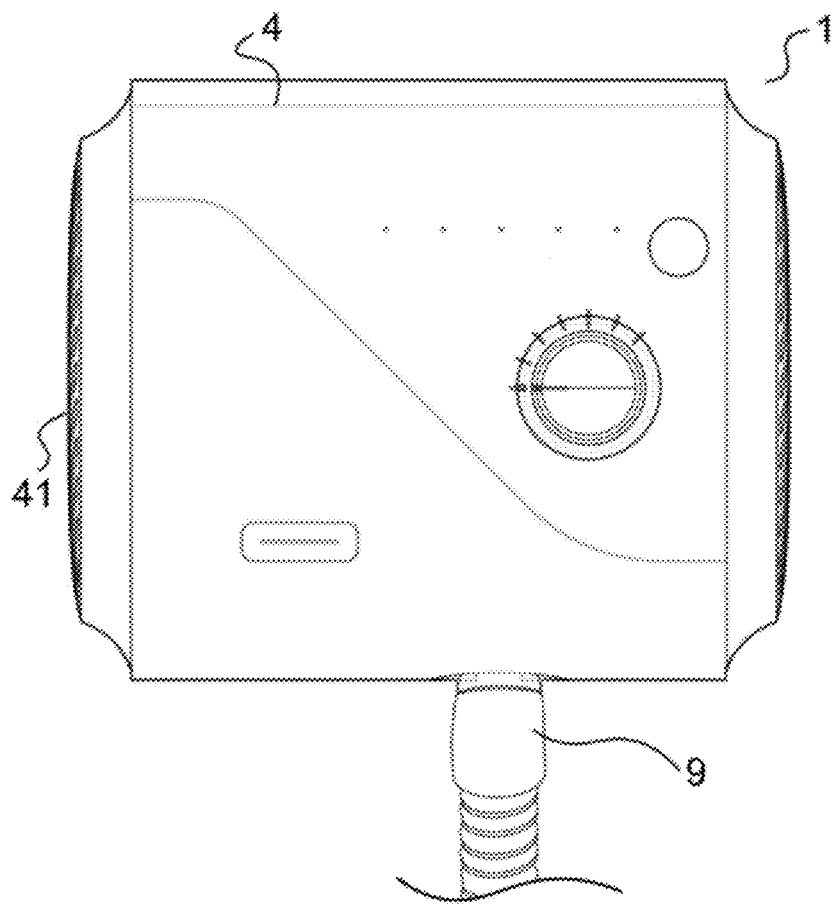
FIG. 3 is a top view of the noise-reducing respiratory device according to an embodiment of the present disclosure.
Figure 4:
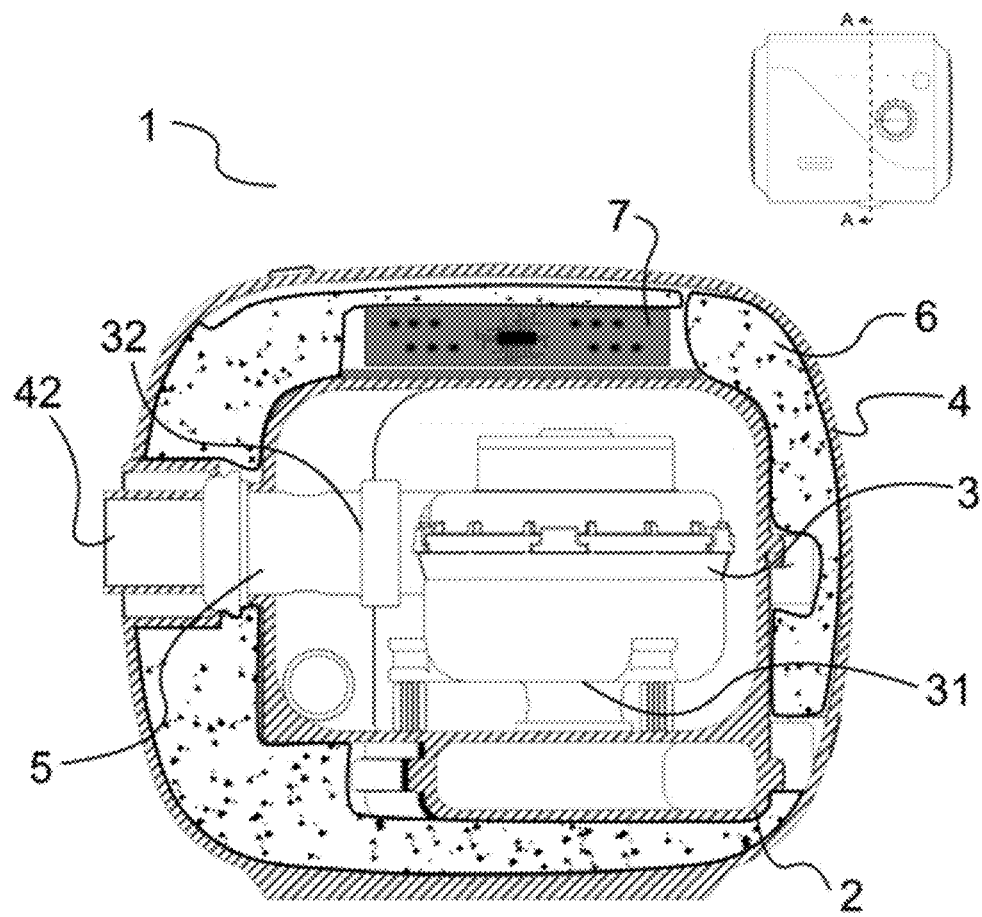
FIG. 4 is a sectional view of the noise-reducing respiratory device according to an embodiment of the present disclosure.
Figure 5:
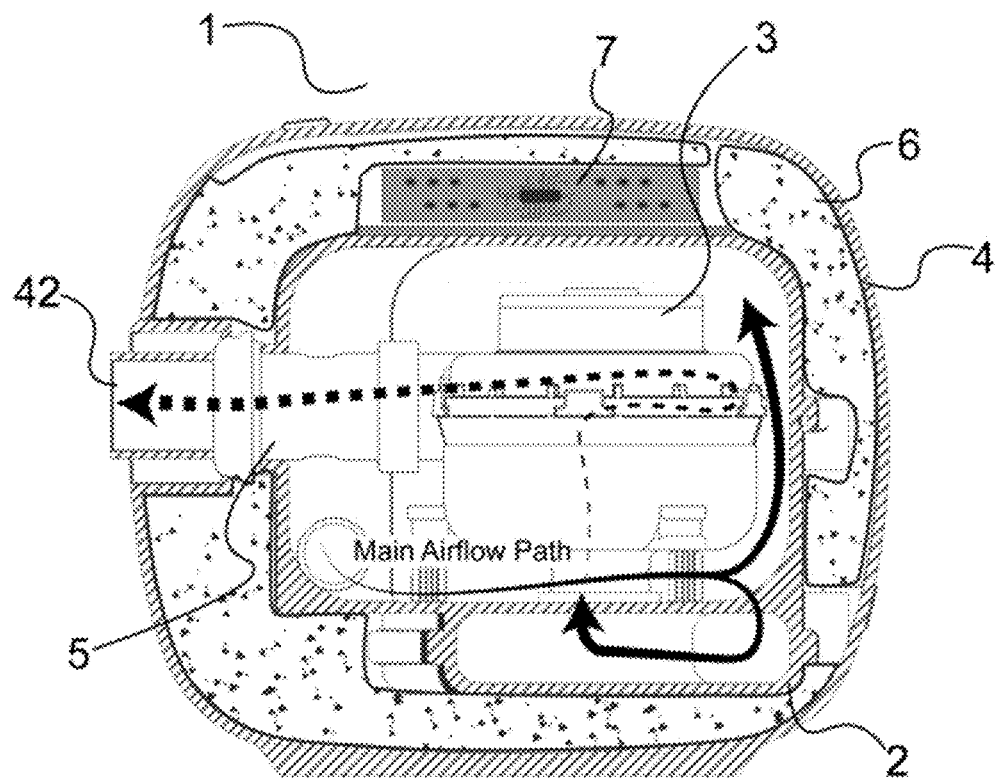
FIG. 5 is a diagram of an airflow path in the noise-reducing respiratory device according to an embodiment of the present disclosure.

To facilitate an understanding of the disclosure, a more comprehensive description will be provided with reference to the accompanying drawings, which illustrate typical embodiments of the disclosure. However, it should be understood that the disclosure can be implemented in many different forms and is not limited to the embodiments described herein. Instead, these embodiments are provided to ensure that this disclosure is thorough and complete.

Unless otherwise defined, all technical and scientific terms used herein have the same meaning as commonly understood by one of ordinary skill in the art to which this disclosure belongs. The terminology used in the description of the disclosure herein is for the purpose of describing particular embodiments only and is not intended to limit the disclosure.

This disclosure addresses existing respiratory devices on the market that commonly use foam for noise reduction within the noise-reducing gas passage. Considering the issues associated with this method—such as foam being prone to damage and aging, posing health risks to patients, complicating manufacturing processes, and being environmentally unfriendly—this disclosure provides a safer, more reliable, and easier to maintain respiratory device. The respiratory device described herein not only optimizes various disadvantages of the existing designs but also ensures that the overall device meets the regulatory noise level standards, making it a superior technological innovation for patients, producers, and the market. The choice of not using foam inside the noise-reducing gas passage and instead placing it between the noise-reducing gas passage and the casing of the device represents a sustainable, environmentally friendly design.

Described below are several structures of the noise-reducing respiratory device according to specific embodiments of this disclosure.

Embodiment 1

This embodiment provides a noise-reducing respiratory device 1. This embodiment includes a three-dimensional schematic diagram, exploded structural view, sectional structure diagram, airflow pathway schematic diagram, and volume comparison schematic diagram, as shown in FIGS. 1-9. This embodiment concerns a noise-reducing respiratory device 1 configured to supply patients with continuous breathable positive pressure gas for treating respiratory system-related disorders such as sleep apnea. The device includes a noise-reducing gas passage 2 and a blower 3 with an inlet 31 and an outlet 32, configured to continuously pressurize the incoming breathable gas to form breathable positive pressure gas. The noise-reducing gas passage 2 is surrounded by a casing 4 of the device, which has at least one air intake 41 and at least one air outlet 42, with soundproofing material 6 positioned between the noise-reducing gas passage 2 and the casing 4 of the device.

Specifically, the casing 4 of the device has at least one air intake 41 and at least one air outlet 42. The air intake 41 is configured to receive breathable gas into the noise-reducing gas passage 2 to supply the blower 3 with sufficient flow of breathable gas for generating breathable positive pressure gas. The air intake 41 on the casing 4 of the device is critical for providing an adequate flow of breathable gas to the noise-reducing gas passage 2; therefore, the casing 4 of the device can have a larger opening for air intake 41 or multiple smaller openings composing the air intake 41. In one implementation, the casing 4 of the device has two or more air intakes 41, which can vary in shape, such as circular, oval, square, or any other form. The air outlet 42 is configured to communicate on one side with the outlet 32 of the blower 3, and on the other side, it connects to a breathing hose 9 to deliver breathable positive pressure gas to the patient's airway. It should be noted that "connected" can mean that the air outlet 42 is directly connected to the outlet 32 of the blower 3 to transmit breathable gas or that the air outlet 42 is connected to the outlet 32 of the blower 3 through one or more additional components—the air outlet 42 first connecting to one or more of these components before connecting to the outlet 32 of the blower 3. In this embodiment, the axial lines of the air intake 41 and the air outlet 42 on the casing 4 of the device are not on the same horizontal plane, which vertically distances the air intake 41 from the air outlet 42 to prevent mutual interference and serves as a form of the noise-reducing structure. Additionally, the casing 4 of the device is divided into at least two parts interconnectable to form a sealed casing 4 of the device, i.e., the casing 4 of the device is split into at least two sections that connect to form the complete casing 4. The casing 4 of the device includes one of the following materials: polypropylene (PP), polycarbonate (PC), polyethylene terephthalate glycol-modified-1,4-cyclohexanedimethanol ester (PCTG), or polyamide (PA).

Figure 6:
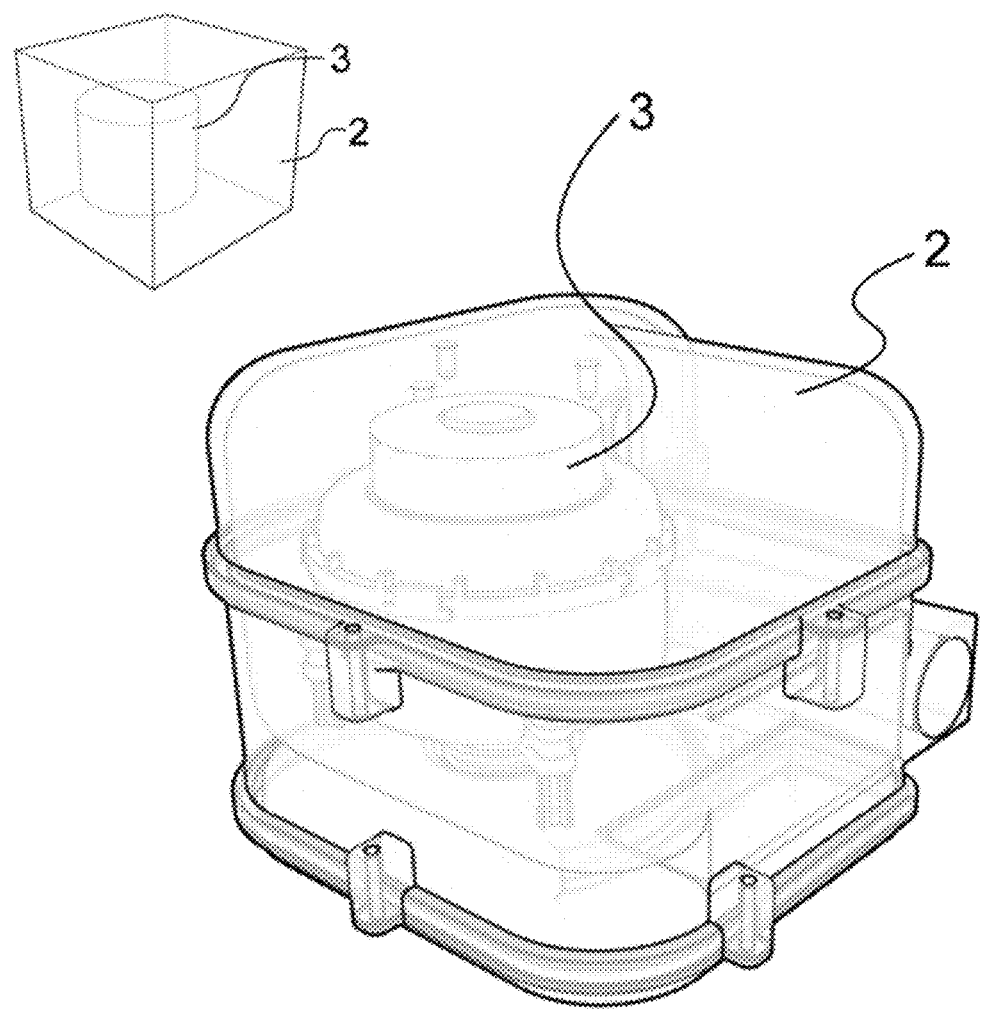
FIG. 6 is a schematic comparison of the volume of a noise-reducing gas passage and a blower within the noise-reducing respiratory device according to an embodiment of the present disclosure.
Figure 7:
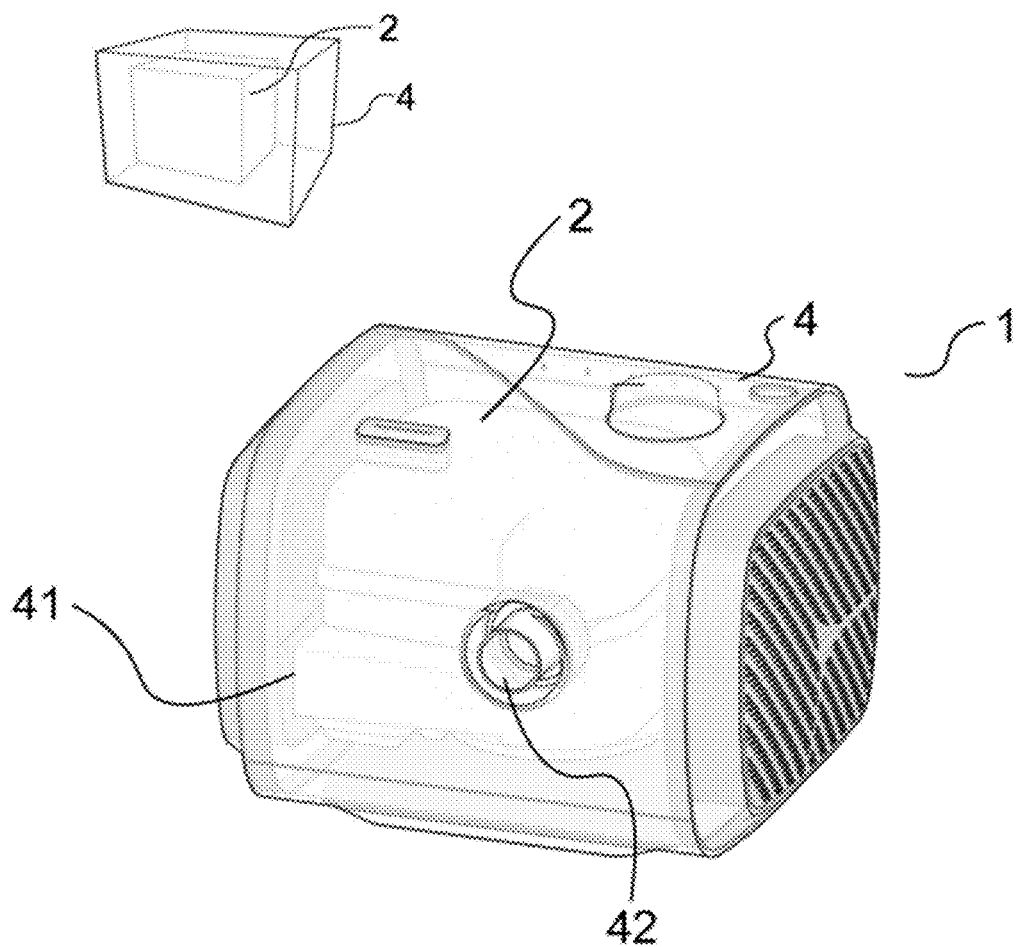
FIG. 7 is a schematic comparison of the volume of the noise-reducing respiratory device and its internal noise-reducing gas passage according to an embodiment of the present disclosure.
Figure 8:
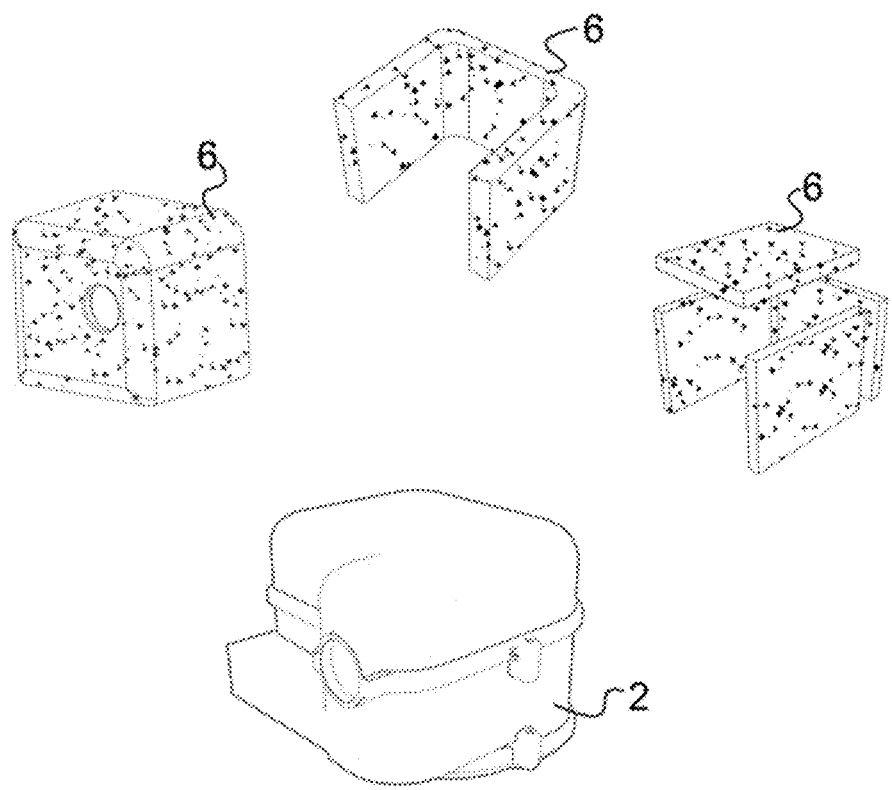
FIG. 8 is a schematic diagram showing different forms of a soundproofing material between a casing and noise-reducing gas passage of the noise-reducing respiratory device according to an embodiment of the present disclosure.

The noise-reducing gas passage 2, connected to the casing 4 of the device, is configured to accommodate the blower 3. In one implementation, the noise-reducing gas passage 2 is sealed to the casing 4 of the device, and this seal is achieved using a sealing component 5. The noise-reducing gas passage 2 is divided into at least two chambers. When the noise-reducing gas passage 2 has two internal chambers, the division of these chambers can be either vertical (top and bottom chambers) or horizontal (side-by-side chambers), with the blower 3 positioned within one of these chambers. Experimental tests on multiple volume ratios between the noise-reducing gas passage 2 and the blower 3 have determined that an optimal internal volume ratio of the noise-reducing gas passage 2 to the volume of blower 3 ranges from 3 to 18, and the ratio of the internal volume of the casing 4 of the device to the interior volume of the noise-reducing gas passage 2 ranges from 1 to 5, as shown in FIGS. 6 and 7. In one implementation, the two chambers include a first chamber and a second chamber inside the noise-reducing gas passage 2, with the blower 3 located in the first chamber, and the path of the gas flow inside the noise-reducing gas passage 2 is free of foam. The blower 3 is positioned within the noise-reducing gas passage 2, where the blower 3 has an inlet 31. To ensure better noise reduction, in one implementation, the inlet 31 of the blower 3 is aligned either parallel or perpendicular to the axis of the air intake 41. In other implementations, the inlet 31 of the blower 3 can be positioned anywhere within the noise-reducing gas passage 2. This embodiment structurally enhances noise reduction by extending the airflow path of the breathable positive pressure gas inside the casing 4 of the device, setting the shortest path of the breathable positive pressure gas from the air intake 41 to the air outlet 42 within the casing 4 of the device to be at least 160 mm. The noise-reducing gas passage includes one of the following materials: polypropylene (PP), polycarbonate (PC), polyethylene terephthalate glycol-modified-1,4-cyclohexanedimethanol ester (PCTG), or polyamide (PA).

Figure 9:
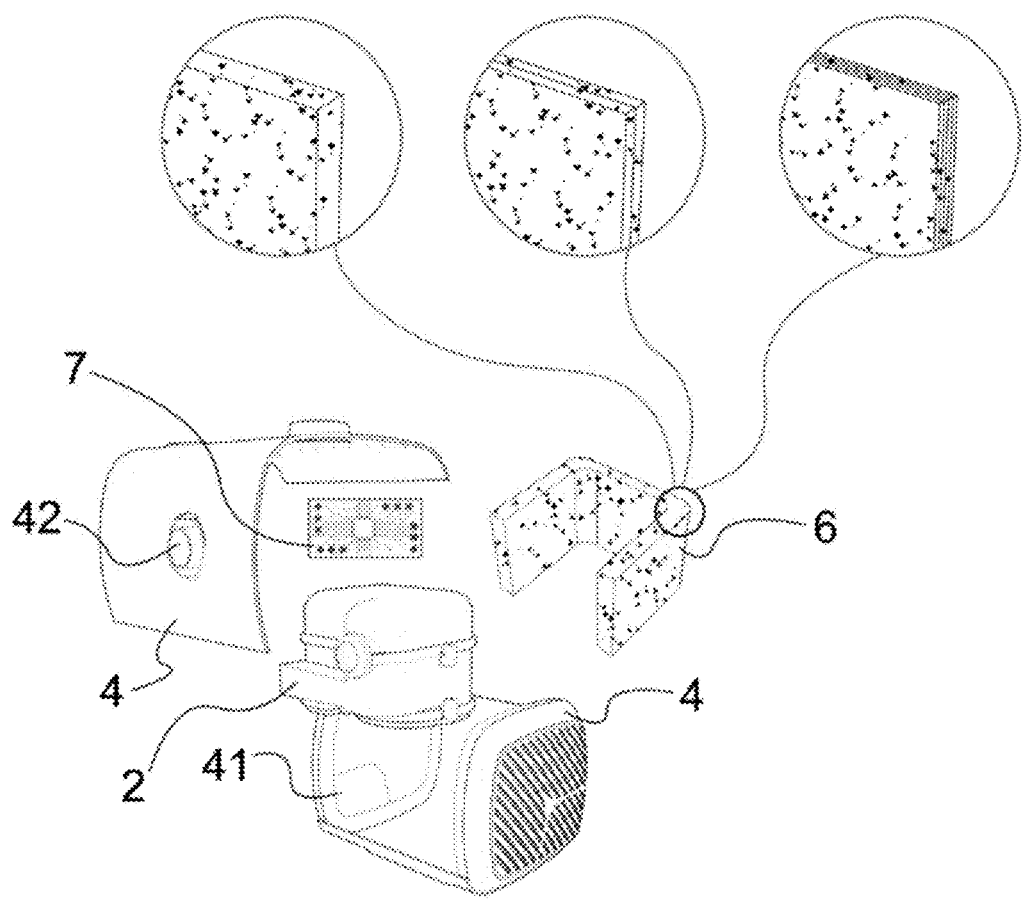
FIG. 9 is a schematic diagram showing different layers of the soundproofing material in the casing and noise-reducing gas passage of the noise-reducing respiratory device according to an embodiment of the present disclosure.

The noise-reducing gas passage 2, having a soundproofing material 6 between it and the casing 4 of the device, is configured to provide the noise-reducing gas passage 2 with noise reduction, vibration damping, and to secure the noise-reducing gas passage 2 within the casing 4 of the device. Compared to placing foam inside the gas passage, positioning the soundproofing material 6 between the noise-reducing gas passage 2 and the casing 4 of the device not only reduces noise but also enhances the safety for the patient. The breathable gas enters from the air intake 41 into the chambers of the noise-reducing gas passage 2, undergoes pressurization and noise reduction, and finally exits through the air outlet 42, all without direct contact with the soundproofing material 6. This design ensures that the airflow is not affected by any potential contaminants from the soundproofing material 6, thereby maintaining the flow's smoothness and purity. During the noise reduction process, the soundproofing material 6, located between the noise-reducing gas passage 2 and the casing 4 of the device, is fixed in place (or potentially glued, taped, or hooked), and it also absorbs the energy from vibrations caused by the blower 3 within the noise-reducing gas passage 2, providing buffering and noise insulation to the noise-reducing gas passage 2 and achieving a noise reduction of at least 2 decibels. The design of this disclosure not only protects the airflow from erosion and contamination by the soundproofing material 6 but also ensures stability and efficacy during the noise reduction process of the airflow. Additionally, the soundproofing material 6 between the noise-reducing gas passage 2 and the casing 4 of the device can take various forms. In one implementation, multiple layers of the soundproofing material 6 are provided (as shown in FIG. 9), with the soundproofing material 6 surrounding at least three sides of the noise-reducing gas passage 2. Furthermore, the soundproofing material 6 is placed between the noise-reducing gas passage 2 and the casing 4 of the device after being molded, which can involve cutting the soundproofing material 6 to shape, forming it integrally or molding, or punch molding before placement. The choice of foam significantly affects the noise reduction performance of the entire respiratory device 1. To optimize noise reduction within the noise-reducing gas passage 2, specific requirements for the foam include a thickness between 3 mm to 25 mm, a hardness between 20 F to 150 F (measured using an Asker F type durometer), and a density between 35 kg/m$^3$ to 150 kg/m$^3$. In addition to the soundproofing material 6, there are also electronic components 7 located between the casing 4 of the device and the noise-reducing gas passage 2, including printed circuit boards, power supplies, and indicator signals. These electronic components 7 can be mounted on the casing 4 of the device or positioned on the noise-reducing gas passage 2.

Figure 10:
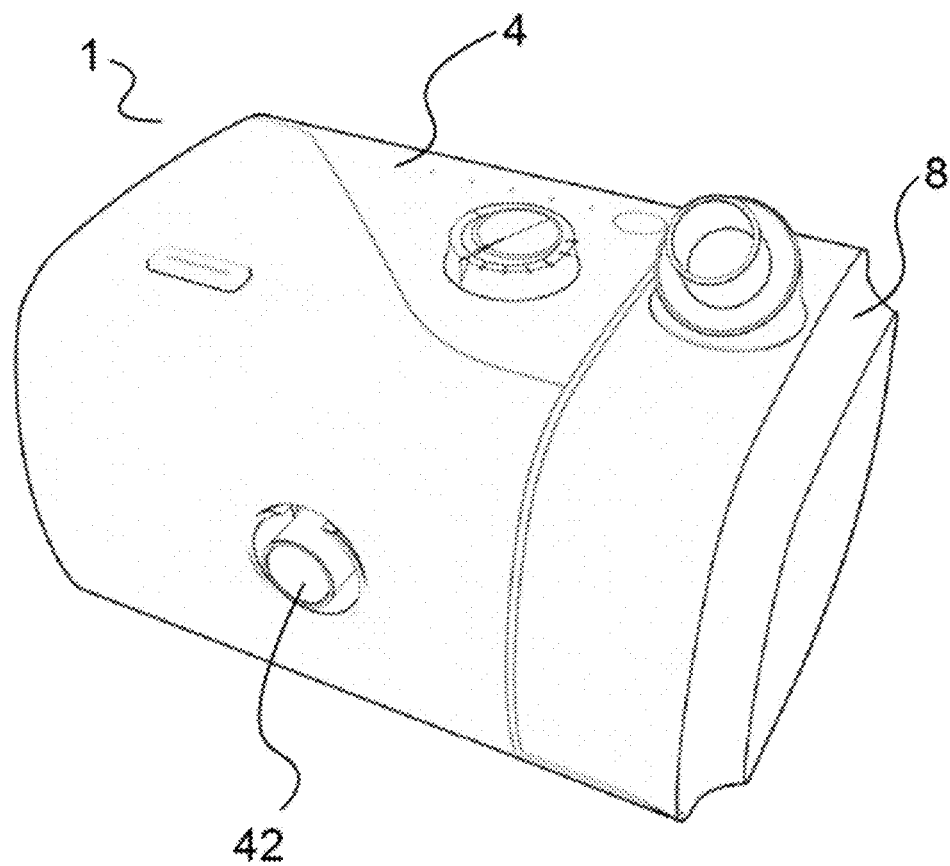
FIG. 10 is a schematic diagram of a noise-reducing respiratory device with a humidifying component according to another embodiment of the present disclosure.

In another embodiment, the respiratory device 1 also includes a humidifying component 8 (as shown in FIG. 10).

Embodiment 2

Figure 11:
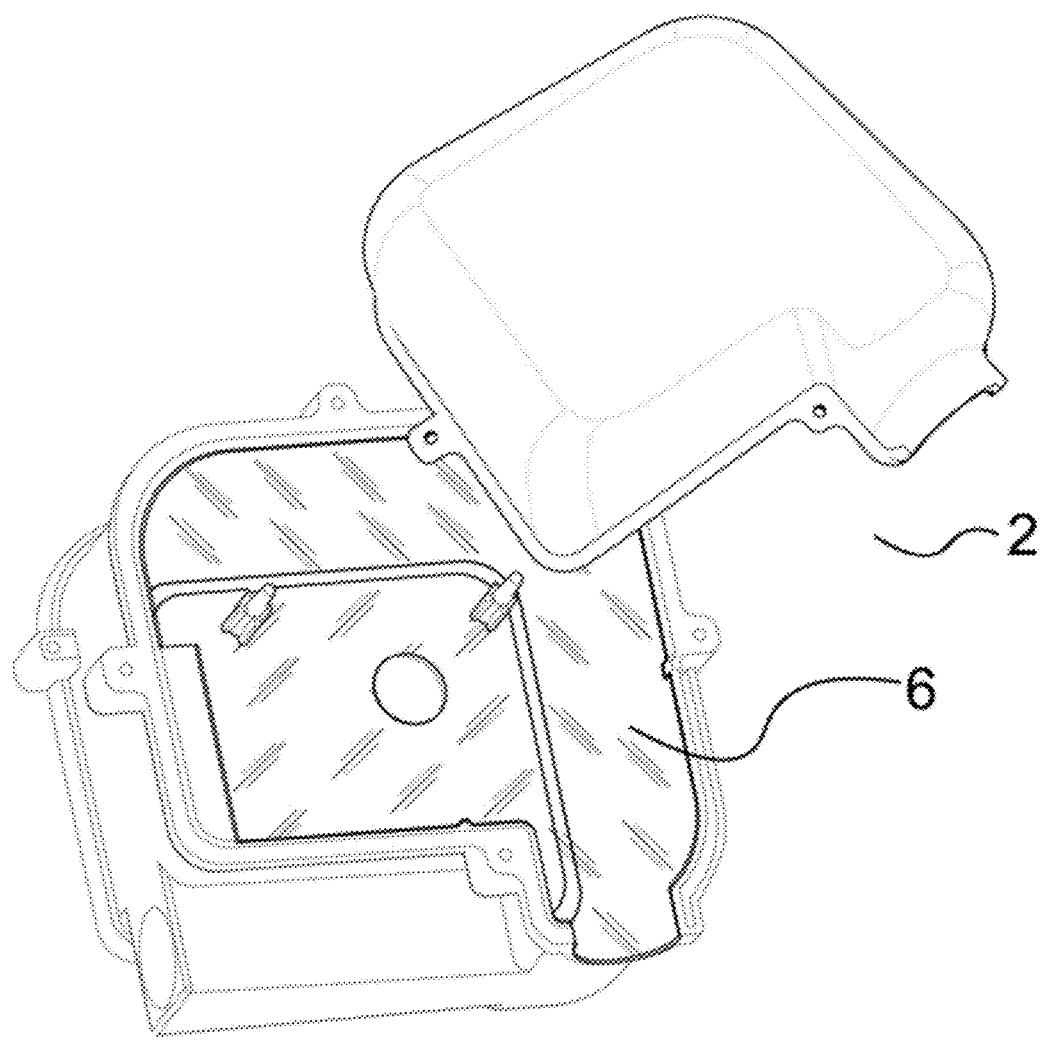
FIG. 11 is a schematic diagram of the noise-reducing respiratory device with a soundproofing material inside a noise-reducing gas passage according to another embodiment of the present disclosure.
Figure 12:
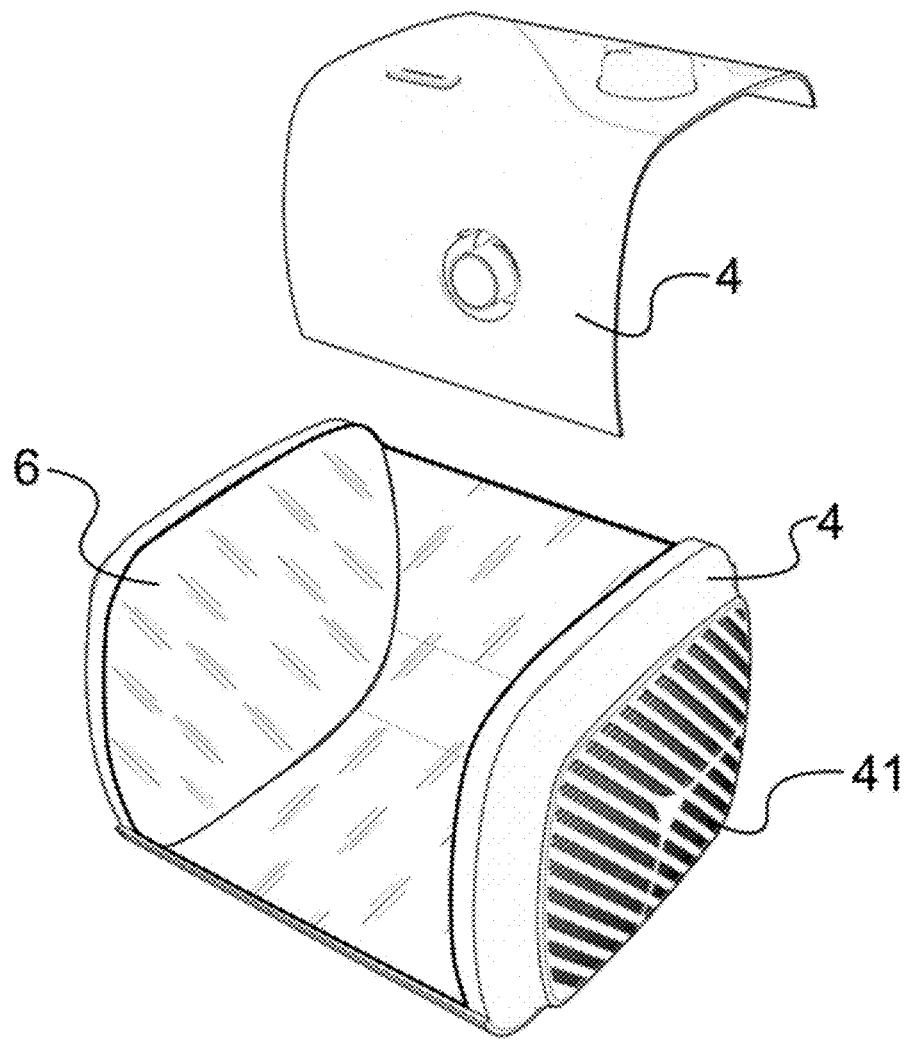
FIG. 12 is a schematic diagram of the noise-reducing respiratory device with the soundproofing material between the noise-reducing gas passage and a casing of the device according to another embodiment of the present disclosure.

This embodiment provides a noise-reducing respiratory device 1, with reference to FIGS. 11-12, offering three-dimensional schematic diagrams. In this embodiment, based on the noise-reducing gas passage 21 from Embodiment 1, the soundproofing material 6 is further specified to be composed of one of the following materials: foam, rubber, silicone, or gel. In one implementation, the soundproofing material 6 is foam, including one of polyurethane foam, polyester foam, polyether foam, neoprene, or cross-linked polyethylene. The soundproofing material 6 is provided either inside the noise-reducing gas passage 2 (where the soundproofing material 6 is not foam, as shown in FIG. 11) or between the noise-reducing gas passage 2 and the casing 4 of the device (as shown in FIG. 12). The primary reason for placing foam inside the respiratory devices 1 on the current market is foam's excellent noise reduction capability and its cost-effectiveness. Specifically, the porous structure within the foam can repeatedly reflect and refract sound waves, causing the sound waves to gradually attenuate and disperse within the porous structure, thereby reducing noise levels. Another characteristic of foam is its elasticity and softness, which allows it to absorb the energy from vibrations caused by the blower 3, converting it into heat energy to dissipate, thereby damping the internal vibrations and noise within the noise-reducing gas passage 2, resulting in a quieter internal airway environment. Similarly, materials such as silicone and gel, which share properties with foam, are used in this embodiment as replacements for foam. Compared to foam, silicone and gel materials are more durable and stable; they do not age or decompose over a long period of time, so using these materials in the noise-reducing respiratory device 1 eliminates concerns about debris and decomposition. Additionally, silicone and gel materials are easier to maintain and less likely to harbor bacteria and mold, contributing to the hygiene and safety of the respiratory device 1. Moreover, silicone and gel materials possess better high-temperature resistance and chemical corrosion resistance, making them suitable for a wider range of environmental conditions. Therefore, in specific situations, replacing foam with silicone or gel materials can better meet the noise reduction needs of respiratory devices and provide more durable and reliable noise reduction effects.

Figure 13:
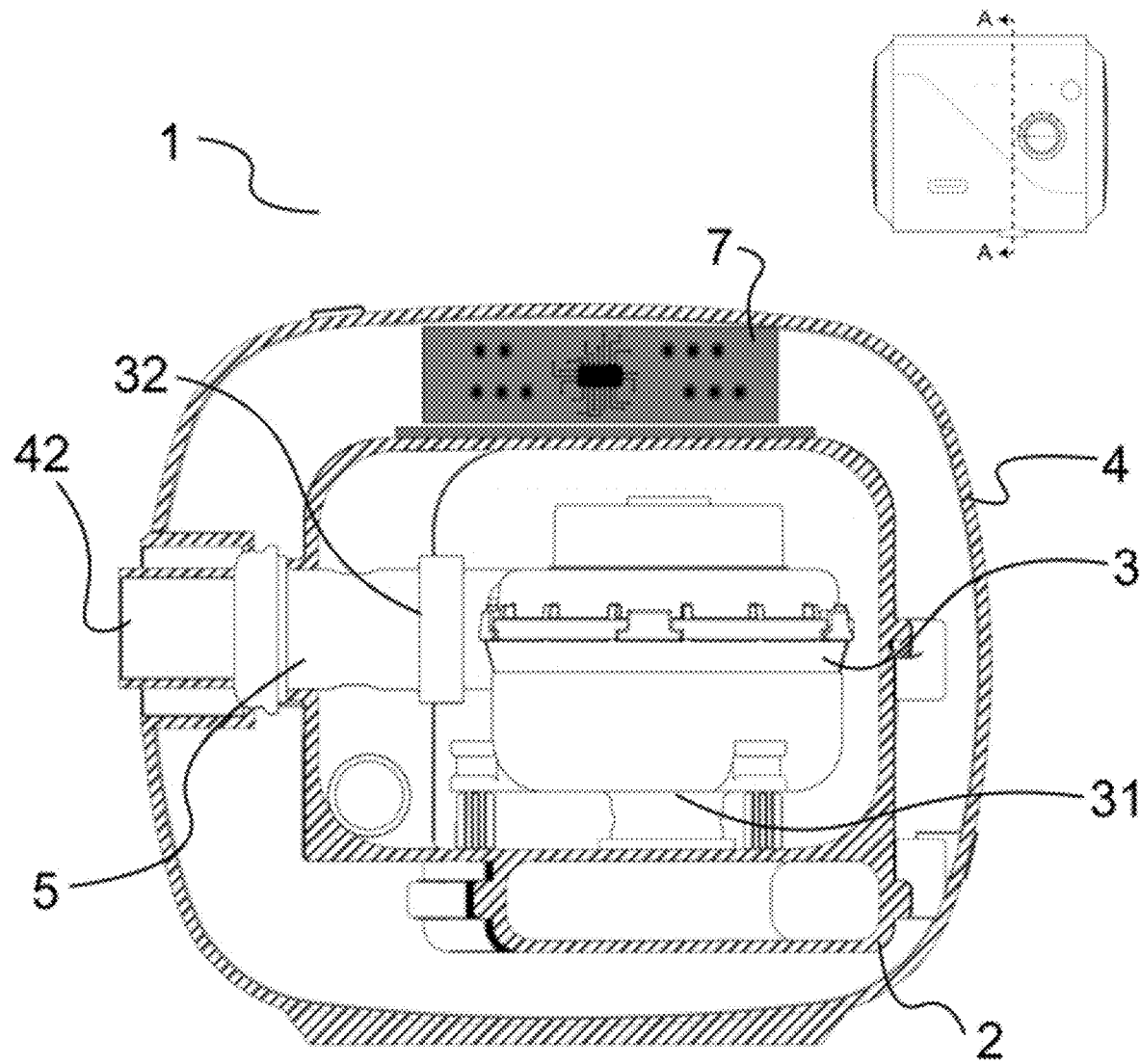
FIG. 13 is a schematic diagram of the noise-reducing respiratory device without the internal soundproofing material, according to another embodiment of the present disclosure.

In another embodiment, the interior of the respiratory device 1, including inside the noise-reducing gas passage and between the noise-reducing gas passage and the casing of the device, may also be devoid of any soundproofing material 6 (such as foam or silicone) (as shown in FIG. 13).

Embodiment 3

Figure 14:
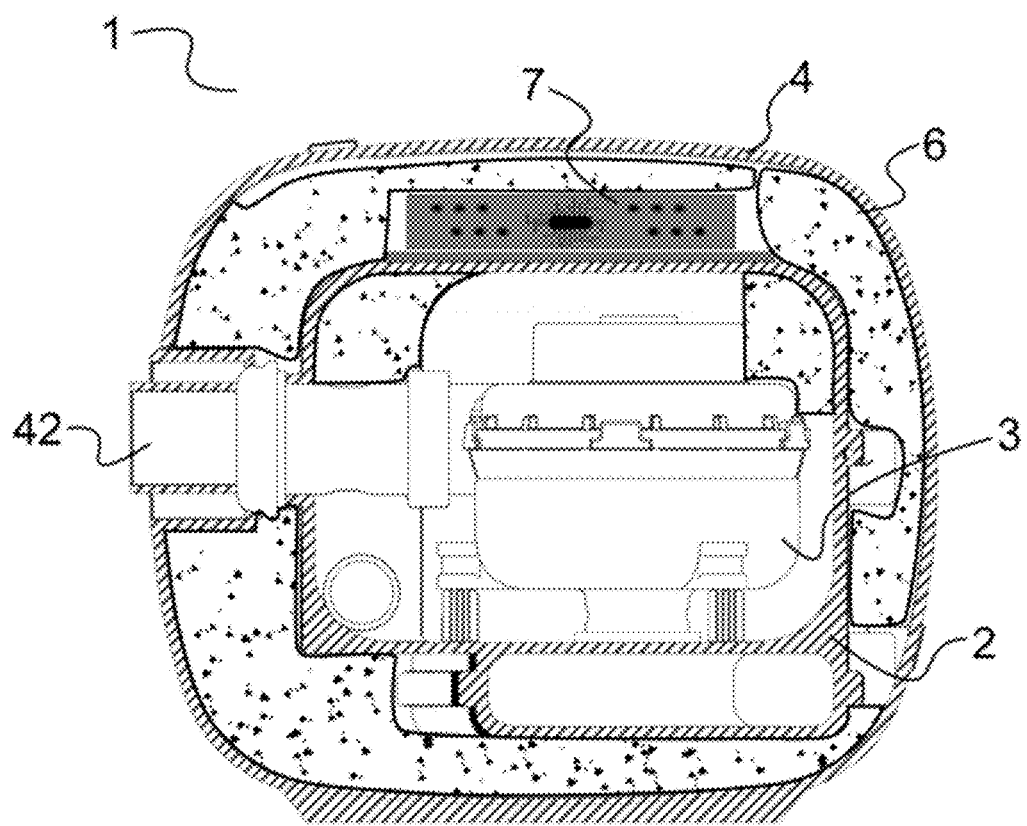
FIG. 14 is a schematic diagram of the noise-reducing respiratory device with foam inside the noise-reducing gas passage and soundproofing material between the noise-reducing gas passage and the casing of the device according to another embodiment of the present disclosure.

This embodiment provides a noise-reducing respiratory device 1, with reference to FIG. 14. This embodiment offers a sectional diagram of the device. In this embodiment, as depicted in FIG. 14, a distinction from the noise-reducing gas passage 21 in Embodiment 1 is that foam is provided within the internal noise-reducing gas passage to achieve noise reduction. While ensuring safety, the respiratory device 1 with foam in the noise-reducing gas passage 2 provides patients with more options. Particularly in today's society, where increasing numbers of people exhibit symptoms of snoring and even suffer from respiratory system-related disorders such as sleep apnea, the demand for respiratory devices 1 is gradually increasing. In this context, patients may have stricter requirements for respiratory device 1; for instance, some patients might need or prefer quieter respiratory devices than those currently available on the market. Therefore, under the premise of ensuring patient safety, this embodiment introduces foam into the noise-reducing gas passage 2. Since this disclosure's noise-reducing device already meets regulatory noise levels even without internal foam, the presence of foam within the noise-reducing gas passage 2 can further convert vibrations inside the noise-reducing gas passage 2 into other forms of energy, while stabilizing airflow to reduce local turbulence, thereby helping to distribute the airflow more evenly. Thus, introducing foam inside the noise-reducing gas passage 2 further reduces the noise level of the respiratory device 1, creating a quieter noise-reducing respiratory device than those currently available on the market, thereby meeting the diverse needs of different patients. This approach makes the noise-reducing respiratory device 1 of this technical disclosure more flexible, able to satisfy the personalized needs of different patients, and provide a more comfortable therapeutic experience.

Embodiment 4

Figure 15:
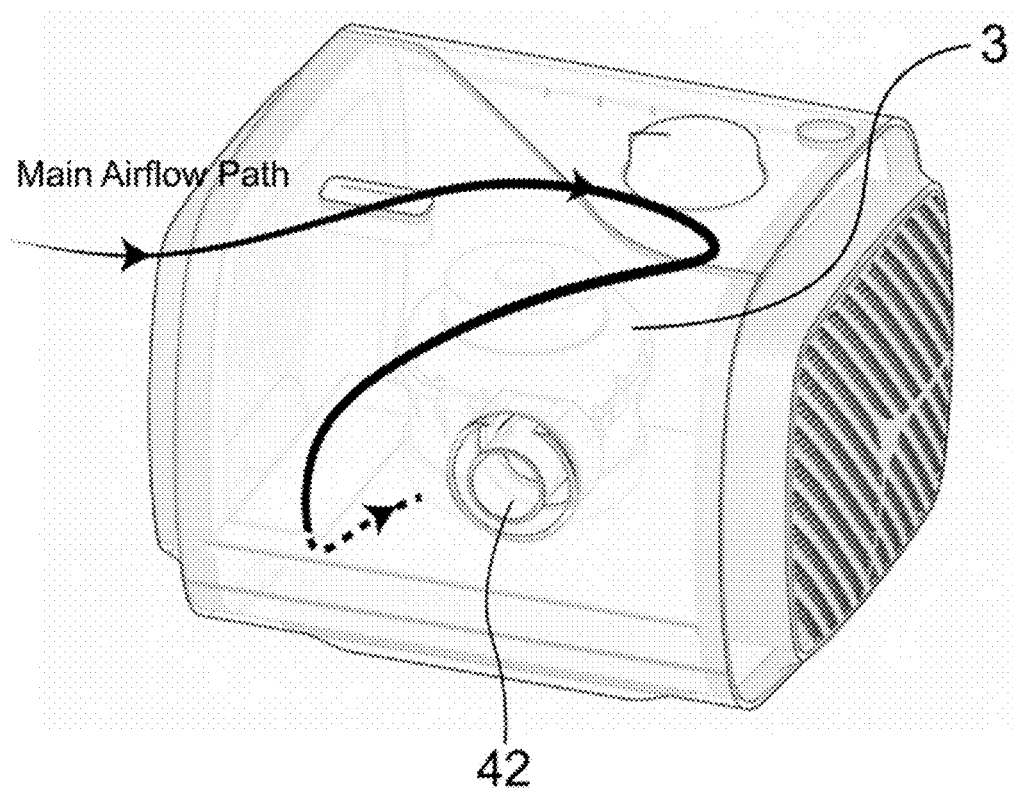
FIG. 15 is a three-dimensional schematic diagram of a part of the respiratory device composed of the casing of the noise-reducing gas passage according to another embodiment of the present disclosure.
Figure 16:
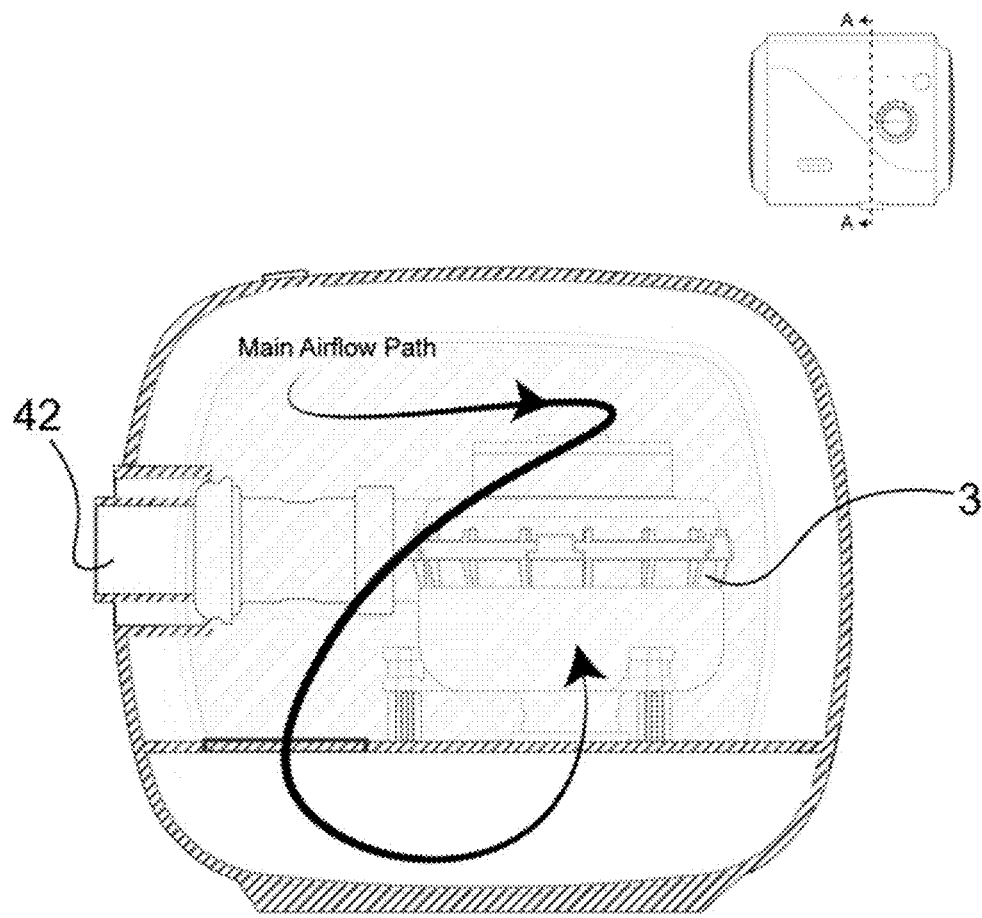
FIG. 16 is a sectional view of a part of the respiratory device composed of the casing of the noise-reducing gas passage, according to another embodiment of the present disclosure.

This embodiment provides a noise-reducing respiratory device 1, with reference to FIGS. 15 and 16. This embodiment offers sectional diagrams of the device. In the embodiment shown in FIGS. 15 and 16, a distinction from the noise-reducing gas passage 2 in Embodiment 1 is that the noise-reducing gas passage 2 and the casing 4 of the device together form the space through which the gas flows. This can also be understood to mean that at least part of blower 3 is exposed inside the casing of the respiratory-related device, i.e., at least part of the casing 4 of the noise-reducing gas passage 2 is the same part as the casing of the respiratory-related device. The term "at least partially" can specifically mean that the casing 4 of the noise-reducing gas passage 2 may completely be the same part as the casing of the respiratory device, or it may be that half or more or less of the casing 4 of the noise-reducing gas passage is the same part as the casing of the respiratory device. FIGS. 15 and 16 illustrate schematic diagrams where the casing 4 of the noise-reducing gas passage 2 is completely the same part as the casing of the respiratory device. This configuration of the respiratory device reduces the device's volume while meeting noise reduction requirements, making the device suitable for specific use scenarios, such as situations where some patients may need to frequently carry the device. The smaller volume ensures that these patients can continue their treatment for respiratory disorders under special circumstances, aiding in the compliance with the device's treatment. This approach also simplifies the device's structure by reducing the number of connections between the casing 4 of the device and the casing 4 of the noise-reducing gas passage 2, which is more advantageous in terms of manufacturing and later maintenance.

The implementation of the respiratory device discussed herein offers at least the following beneficial effects:

1. The design of a foam-free noise-reducing gas passage device enhances the safety of respiratory-related devices. In 2021, a globally renowned brand issued its first worldwide recall notice involving some of its Bi-level Positive Airway Pressure (BiPAP) devices, Continuous Positive Airway Pressure (CPAP) devices, and mechanical ventilators, followed by several more recalls. The main reason for the recall was the inappropriate use of sound-absorbing foam within the noise-reducing gas passage, which could potentially release particles and organic compounds. In 2023, the FDA received thousands of complaints about this internationally known brand's CPAP and BiPAP machines. This incident had a significant negative impact on the brand's reputation.

The FDA requires that ventilators must demonstrate a noise level below 30 dB for market approval. Using foam for noise reduction is currently the simplest method because foam materials are easily obtainable and manufacturable. Their unique porous structure and material properties can convert noise into minimal energy, thereby reducing noise.

Indeed, using foam to reduce noise can achieve a good noise reduction effect, and placing foam inside the noise-reducing gas passage device is the simplest, most effective, and common means to meet regulatory noise standards.

Therefore, nearly all respiratory-related machines on the current market incorporate foam within the gas passage for noise reduction. However, foam can easily cause health issues for several reasons:

D. Due to the softness and relatively loose surface of foam materials, they can be easily worn away or peeled off by airflow during use, releasing particles. Once released, these particles can easily enter the patient's airway with the airflow, irritating the respiratory system. This may cause respiratory problems, leading to symptoms such as sore throat and coughing, especially in individuals already suffering from respiratory diseases such as asthma or Chronic Obstructive Pulmonary Disease (COPD).

E. Additionally, foam is often made from synthetic materials that may contain residual chemical additives. These chemicals can gradually be released as the foam ages and degrades. In some cases, if foam particles carry harmful microbes, they could lead to potential infections, particularly in individuals with weakened immune systems. Foam particles may also trigger allergic reactions, including sneezing, flu-like symptoms, and eye irritation.

F. Furthermore, foam used over long periods can accumulate dust, bacteria, and other contaminants, especially in respiratory devices. The device can easily inhale contaminants from the air, leading to bacterial growth and increasing the risk of infection.

The disclosure discussed herein specifically focuses on the safety and reliability of the ventilator's noise-reducing gas passage during design, implementing a series of stringent safety measures, including a foam-free design of the noise-reducing gas passage device, to reduce potential health risks to patients using ventilators. In designing the gas passage and filtration system, foam-free or easily replaceable foam designs are used to mitigate these potential health risks. For patient health and safety, the gas passage is configured to be foam-free. Since there is no foam in the gas passage, it reduces the chance of accumulating minute foreign objects, helping to maintain cleanliness in the gas passage. More importantly, the air breathed is not affected by minute residues from the foam itself, lowering the number of particles that patients might inhale or come into contact with, ensuring safety during device use. This is particularly important for patients who use the device over a long period as it helps to reduce potential respiratory issues. Additionally, some patients may be allergic to particles from materials such as foam, and the foam-free design reduces the risk associated with allergic reactions. This is also crucial for those allergic to foam materials or sensitive to chemically treated materials. Through multiple tests, this product has demonstrated that the foam-free noise-reducing gas passage device can enhance patient safety and comfort during device use.

2. Besides ensuring noise reduction, respiratory devices actually specify the pressure and flow of the gas blown into the patient's airway. Placing foam within the noise-reducing gas passage may cause some of the gas to be absorbed by the foam, resulting in the blown-out gas not meeting the required flow or pressure standards. The primary reasons foam can lead to inadequate pressure and flow include its porous structure, which slows down the gas velocity as it passes through the pores, increasing gas resistance and likely reducing pressure. Additionally, the foam may absorb some of the gas, thus reducing the flow rate of the gas exiting the respiratory device. Moreover, after prolonged use, the foam may become contaminated with dust, bacteria, and other substances, leading to clogged pores and further increasing airflow resistance, thus degrading the gas flow performance. Therefore, considering all these factors, this disclosure employs only the internal structure or components within the noise-reducing gas passage for noise reduction, without absorbing or obstructing the airflow. It relocates the soundproofing material from inside the air passage chamber to between the noise-reducing gas passage and the casing of the device, ensuring that the airflow does not pass through foam. In this position, the soundproofing material functions to absorb the energy and noise generated by the vibrations of the noise-reducing gas passage, thereby preventing its transmission to the casing of the device and the external environment, reducing external noise disturbances to the patient. Furthermore, the soundproofing material between the casing of the device and the noise-reducing gas passage also serves to stabilize the air passage within the casing, maintaining the stability and durability of the respiratory device to ensure lasting and stable therapeutic effects. This design of placing the soundproofing material between the noise-reducing gas passage and the casing of the device not only effectively avoids obstruction of the airflow by the soundproofing material but also maximizes its noise reduction and stabilizing functions, providing patients with a quieter and more comfortable breathing environment.

3. The soundproofing material positioned between the noise-reducing gas passage and the casing of the device not only reduces noise and enhances safety but also serves multiple other functions. (1) The use of soundproofing material outside the chamber not only reduces noise and enhances safety but also provides dual-buffering shock absorption (during use and transport), offering comprehensive protection for the device's stable operation and the patient's comfort. a. Firstly, the soundproofing material between the noise-reducing gas passage and the casing of the device can serve the same function as foam inside the air passage, while also minimizing the risk of gas passing through foam. The soundproofing material between the air passage and the casing allows the respiratory device to reduce noise generated by vibrations of the noise-reducing gas passage, converting sound waves into other forms of energy absorbed by the soundproofing material. Therefore, it isolates noise within the device casing, providing buffering for the noise-reducing gas passage during use. b. The soundproofing material also serves as a buffer during transport; during transportation, the device may be subjected to bumps and vibrations, and soundproofing materials (such as foam and silicone) as relatively soft materials can absorb and mitigate external shocks to some extent, protecting the internal structure of the device, especially the noise-reducing gas passage and its internal components, making the transportation of the respiratory device safer and more reliable. (2) On one hand, since breathable positive pressure gas does not pass through the soundproofing material, the selection of soundproofing material does not need to consider factors such as the potential release of harmful gases into the airflow, which broadens the range of choices for the soundproofing material and further controls the manufacturing costs of the respiratory device to some extent. (3) With foam already installed inside the noise-reducing gas passage, adding further soundproofing material between the casing of the device and the noise-reducing gas passage makes the device even quieter, surpassing regulatory noise level standards. By combining the use of foam within the noise-reducing gas passage and soundproofing material between the casing of the device and the noise-reducing gas passage, the respiratory device maintains its original functions and performance while achieving dual noise reduction, creating a more tranquil and comfortable therapeutic environment for patients.

It must be noted that as used herein and in the appended claims, the regular forms "a" "an" "the" include their plural equivalents, unless the context clearly dictates otherwise.

The invention claimed is:

1. A noise-reducing respiratory device configured to provide continuous breathable positive pressure gas to a patient to treat respiratory system-related disorders, the noise-reducing respiratory device comprising:
    a casing configured to include at least one air intake and at least one air outlet;
    a blower having an inlet and an outlet, configured to continuously pressurize breathable gas entering an interior of the noise-reducing respiratory device to form the continuous breathable positive pressure gas;
    a noise-reducing gas passage configured to accommodate the blower, the noise-reducing gas passage being sealably connectable to the casing through a sealing component;
        wherein the noise-reducing gas passage is configured to reduce noise by extending an airflow path of the breathable gas,
        wherein a shortest path for the continuous breathable positive pressure gas inside the casing from the at least one air intake to the at least one air outlet is at least 160 mm,
        the at least one air intake is configured to receive the breathable gas into the noise-reducing gas passage to supply the blower with the breathable gas to generate the continuous breathable positive pressure gas, and
        the at least one air outlet is configured on one side to communicate with the outlet of the blower, and configured on another side to connect to a breathing hose to provide the continuous breathable positive pressure gas to the patient's airway;
    electronic components provided between the casing and the noise-reducing gas passage; and
    a soundproofing material provided outside the noise-reducing gas passage between the noise-reducing gas passage and the casing,
        wherein a ratio of an interior volume of the noise-reducing gas passage to a volume of the blower is between 3 to 18, and a ratio of an internal volume of the casing to the interior volume of the noise-reducing gas passage is between 1 to 5, and
    the device is configured to provide the breathable gas to the patient through the connected breathing hose during sleep treatment.

2. The noise-reducing respiratory device according to claim 1, wherein the noise-reducing gas passage includes a first chamber and a second chamber.

3. The noise-reducing respiratory device according to claim 2, wherein the blower is provided in the first chamber.

4. The noise-reducing respiratory device according to claim 1, wherein the inlet of the blower is parallel or perpendicular to an axis of the at least one air intake.

5. The noise-reducing respiratory device according to claim 1, wherein the soundproofing material comprises at least one material selected from the group consisting of foam, rubber, and silicone.

6. The noise-reducing respiratory device according to claim 1, wherein the noise-reducing gas passage and the casing form a space through which the breathable gas flows.

7. A noise-reducing respiratory device configured to provide continuous breathable positive pressure gas to a patient to treat respiratory system-related disorders, the noise-reducing respiratory device comprising:
    a casing configured to include at least one air intake and at least one air outlet;
    a blower having an inlet and an outlet, configured to continuously pressurize breathable gas entering an interior of the noise-reducing respiratory device to form the continuous breathable positive pressure gas;
    a noise-reducing gas passage configured to accommodate the blower and be connectable to the casing;
        wherein the noise-reducing gas passage is configured to reduce noise by extending an airflow path of the breathable gas,
        wherein a shortest path for the continuous breathable positive pressure gas inside the casing from the at least one air intake to the at least one air outlet is at least 160 mm,
        the at least one air intake is configured to receive the breathable gas into the noise-reducing gas passage to supply the blower with the breathable gas to generate the continuous breathable positive pressure gas, and
        the at least one air outlet is configured on one side to communicate with the outlet of the blower, and configured on another side to connect to a breathing hose to provide the continuous breathable positive pressure gas to the patient's airway;
    electronic components provided between the casing and the noise-reducing gas passage; and
    a soundproofing material provided outside the noise-reducing gas passage between the noise-reducing gas passage and the casing,
        wherein the soundproofing material is configured to include foam and has at least one of the following characteristics:
            a. a thickness between 3 mm to 25 mm;
            b. a hardness between 20 F to 150 F;
            c. a density between 35 kg/m$^3$ to 150 kg/m$^3$,
        wherein a ratio of an interior volume of the noise-reducing gas passage to a volume of the blower is between 3 to 18, and a ratio of an internal volume of the casing to the interior volume of the noise-reducing gas passage is between 1 to 5, and
    the device is configured to provide the breathable gas to the patient through the connected breathing hose during sleep treatment.

8. The noise-reducing respiratory device according to claim 7, wherein an axis of the at least one air intake of the casing is not on a same horizontal plane as an axis of the at least one air outlet.

9. The noise-reducing respiratory device according to claim 7, wherein multiple layers of the soundproofing material are provided between the noise-reducing gas passage and the casing.

10. The noise-reducing respiratory device according to claim 7, wherein the casing comprises at least one material selected from the group consisting of polypropylene, polycarbonate, polyethylene terephthalate-1,4-cyclohexane dimethanol ester, and polyamide.

11. A noise-reducing respiratory device configured to provide continuous breathable positive pressure gas to a patient to treat respiratory system-related disorders, the noise-reducing respiratory device comprising:
    a casing configured to include at least one air intake and at least one air outlet;

a blower having an inlet and an outlet, configured to continuously pressurize breathable gas entering an interior of the noise-reducing respiratory device to form the continuous breathable positive pressure gas;

a noise-reducing gas passage configured to accommodate the blower and be connectable to the casing;

wherein the noise-reducing gas passage is configured to reduce noise by extending an airflow path of the breathable gas, an interior space of the noise-reducing gas passage through which the breathable gas flows does not include foam, the at least one air intake is configured to receive the breathable gas into the noise-reducing gas passage to supply the blower with the breathable gas to generate the continuous breathable positive pressure gas, and the at least one air outlet is configured on one side to communicate with the outlet of the blower, and configured on another side to connect to a breathing hose to provide the continuous breathable positive pressure gas to the patient's airway;

electronic components provided between the casing and the noise-reducing gas passage; and a soundproofing material provided outside the noise-reducing gas passage between the noise-reducing gas passage and the casing wherein a ratio of an interior volume of the noise-reducing gas passage to a volume of the blower is between 3 to 18, and a ratio of an internal volume of the casing to the interior volume of the noise-reducing gas passage is between 1 to 5, and wherein the device is configured to provide the breathable gas to the patient through the connected breathing hose during sleep treatment.

12. The noise-reducing respiratory device according to claim 11, wherein the inlet of the blower is parallel or perpendicular to an axis of the at least one air intake.

13. The noise-reducing respiratory device according to claim 12, wherein the axis of the at least one air intake is not on a same horizontal plane as an axis of the at least one air outlet.

14. The noise-reducing respiratory device according to claim 11, wherein the noise-reducing respiratory device further comprises a humidifying component.

15. The noise-reducing respiratory device according to claim 11, wherein the casing is configured to be divided into at least two parts, each of the at least two parts being interconnectable to form the integral casing.

16. A noise-reducing respiratory device configured to provide continuous breathable positive pressure gas to a patient to treat respiratory system-related disorders, the noise-reducing respiratory device comprising:

a casing configured to include at least one air intake and at least one air outlet;

a blower having an inlet and an outlet, configured to continuously pressurize breathable gas entering an interior of the noise-reducing respiratory device to form the continuous breathable positive pressure gas;

a noise-reducing gas passage configured to accommodate the blower and be connectable to the casing;

wherein the noise-reducing gas passage is configured to reduce noise by extending an airflow path of the breathable gas, wherein a shortest path for the continuous breathable positive pressure gas inside the casing from the at least one air intake to the at least one air outlet is at least 160 mm, the noise-reducing gas passage is configured to be divided into at least two chambers, the blower being housed within at least one of the at least two chambers, and an interior space of the noise-reducing gas passage through which the breathable gas flows does not include foam, the at least one air intake is configured to receive the breathable gas into the noise-reducing gas passage to supply the blower with the breathable gas to generate the continuous breathable positive pressure gas, and the at least one air outlet is configured on one side to communicate with the outlet of the blower, and configured on another side to connect to a breathing hose to provide the continuous breathable positive pressure gas to the patient's airway;

electronic components provided between the casing and the noise-reducing gas passage; and a soundproofing material provided outside the noise-reducing gas passage between the noise-reducing gas passage and the casing, wherein a ratio of an interior volume of the noise-reducing gas passage to a volume of the blower is between 3 to 18, and a ratio of an internal volume of the casing to the interior volume of the noise-reducing gas passage is between 1 to 5, and the device is configured to provide the breathable gas to the patient through the connected breathing hose during sleep treatment.

17. The noise-reducing respiratory device according to claim 16, wherein the noise-reducing gas passage comprises at least one material selected from the group consisting of polypropylene, polycarbonate, polyethylene terephthalate-1, 4-cyclohexane dimethanol ester, and polyamide.

18. The noise-reducing respiratory device according to claim 16, wherein the soundproofing material, once molded, is provided between the noise-reducing gas passage and the casing.

19. The noise-reducing respiratory device according to claim 16, wherein the casing is configured to be divided into at least two parts, each of the at least two parts being interconnectable to form the integral casing.

20. The noise-reducing respiratory device according to claim 16, wherein the foam includes one of the following materials: polyurethane foam, polyester foam, polyether foam, neoprene, or cross-linked polyethylene.

\* \* \* \* \*